(12) United States Patent
Wild et al.

(10) Patent No.: US 12,268,801 B2
(45) Date of Patent: Apr. 8, 2025

(54) MEDIA SUPPLY ARRANGEMENT FOR SUPPLYING A MEDICAL TREATMENT DEVICE

(71) Applicant: Fresenius Medical Care Deutschland GmbH, Bad Homburg (DE)

(72) Inventors: Michael Wild, Bad Homburg (DE); Andreas Leclerc, Bad Nauheim (DE); Carsten Russ, Bad Vilbel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 701 days.

(21) Appl. No.: 17/273,609

(22) PCT Filed: Sep. 5, 2019

(86) PCT No.: PCT/EP2019/073749
§ 371 (c)(1),
(2) Date: Mar. 4, 2021

(87) PCT Pub. No.: WO2020/049119
PCT Pub. Date: Mar. 12, 2020

(65) Prior Publication Data
US 2021/0361842 A1 Nov. 25, 2021

(30) Foreign Application Priority Data
Sep. 5, 2018 (DE) .......................... 102018121671.8

(51) Int. Cl.
*A61M 1/16* (2006.01)
*A61M 1/36* (2006.01)

(52) U.S. Cl.
CPC ........ *A61M 1/1664* (2014.02); *A61M 1/3607* (2014.02); *A61M 1/3623* (2022.05);
(Continued)

(58) Field of Classification Search
CPC ........ F24F 1/0314; F24F 1/0358; F24F 1/037; F24F 11/50; F24F 11/56; F24F 12/001; A61G 10/02
See application file for complete search history.

(56) References Cited

U.S. PATENT DOCUMENTS 9,265,873 B2   2/2016   Ritter
10,532,140 B2   1/2020   Meierhofer
(Continued)

FOREIGN PATENT DOCUMENTS

CN    105682633    6/2016
DE    202012005708  9/2013
(Continued)

OTHER PUBLICATIONS

English translation of JP 2006-275383.*
(Continued)

*Primary Examiner* — Benjamin M Kurtz
(74) *Attorney, Agent, or Firm* — Fish & Richardson P.C.

(57) ABSTRACT

The present disclosure pertains to a media supply arrangement for supplying a medical treatment device with a medium, in particular for supplying an extracorporeal blood treatment device with a dialysis medium, wherein an air conditioning device for air conditioning of a medical treatment device coupled to the media supply arrangement is provided.

25 Claims, 3 Drawing Sheets

(52) U.S. Cl.
CPC ............... *A61M 2205/3368* (2013.01); *A61M 2205/3553* (2013.01); *A61M 2205/3606* (2013.01)

(56) References Cited

U.S. PATENT DOCUMENTS

2004/0211718 A1   10/2004  Deguchi et al.
2011/0061967 A1*  3/2011  Penner .................... F24F 13/24
                                                              181/224
2019/0083691 A1    3/2019  Gauthier et al.

FOREIGN PATENT DOCUMENTS

| DE | 102014015795 | | 4/2016 | |
|----|--------------|---|--------|---|
| DE | 202017104462 | | 8/2017 | |
| JP | 2006275383 | * | 10/2006 | ................ F24F 3/14 |
| JP | 201780137 | * | 5/2017 | .............. A61M 1/14 |
| TW | M482128 | | 7/2014 | |
| WO | WO 2012/119799 | | 9/2012 | |
| WO | WO 2015/029045 | | 3/2015 | |
| WO | WO 2017/156643 | | 9/2017 | |

OTHER PUBLICATIONS

PCT International Preliminary Report on Patentability in International Appln. No. PCT/EP2019/073749, mailed Mar. 18, 2021, 15 pages (with English translation).
PCT International Search Report and Written Opinion in International Appln. No. PCT/EP2019/073749, mailed Nov. 20, 2019, 19 pages (with English translation).

* cited by examiner

MEDIA SUPPLY ARRANGEMENT FOR SUPPLYING A MEDICAL TREATMENT DEVICE

CROSS-REFERENCE TO RELATED APPLICATIONS

The present application is the national stage entry of International Patent Application No. PCT/EP2019/073749, filed on Sep. 5, 2019, and claims priority to Application No. DE 10 2018 121 671.8, filed in the Federal Republic of Germany on Sep. 5, 2018, the disclosures of which are expressly incorporated herein in their entireties by reference hereto.

TECHNICAL FIELD

The disclosure relates to a media supply arrangement for supplying a medical treatment device with a medium, for example for supplying an extracorporeal blood treatment device with a dialysis medium.

BACKGROUND

Time and again complaints are received in dialysis clinics from patients during dialysis treatments regarding the indoor air comfort. The patients complain about the indoor air temperature being too high or too low, having a too high or too low humidity, poor quality room air, or they feel uncomfortable due to draft effects. These draft effects develop due to the central supply air introduced into the room via an air conditioning or ventilation system.

Generally, each patient and also the personnel perceive the room air condition differently, in particular with regard to the temperature. Dialysis patients that are often seated or in a resting position during the extracorporeal blood treatment have limited movement and often feel cold whereas the personnel interchanges between a seated and standing activity and also changes between rooms, such that they are hence more active and less sensible to cold.

Furthermore, the introduction of fresh air is required for a pleasant indoor climate. To this end windows are often simply opened aside from the air conditioning or ventilation system, wherein the supply air that has previously been energetically conditioned is lost and at the same time noise disturbances may come from outside. The position of the patient in the room is furthermore decisive. When a treatment area is e.g., directly in front of a window or below an air output of the air conditioning system, this may negatively influence the comfort.

In particular in summer, when a cooling requirement already exists due to the outside temperature, the problem of draft effects is present. The cooling requirement is furthermore problematic due to the high internal thermal loads, in particular the heat generation by persons and technical devices, since these thermal loads result in increased volume flows of the air conditioning and ventilation systems and hence intensify the already existing draft effects.

Common solutions based on a central climatization or conditioning of a room by means of central building technologies hence provide no satisfying solution for the different perception of heat and cold of the patients or for the different heat generation of the respective treatment devices, depending on the positioning and treatment phase. Accordingly, a need exists to improve the climatization or air conditioning of treatment rooms and in particular to enable an individual configuration thereof for the respective patient.

SUMMARY

Starting from the known prior art, it is an object of the present disclosure to provide improved comfort for patients that are treated with a medical treatment device.

In some embodiments, this object is achieved with a media supply arrangement as described further below. Preferred embodiments are provided in the present description as well as the Figures.

Accordingly, a media supply arrangement for supplying a medical treatment device with a medium, in particular for supplying an extracorporeal blood treatment device with a dialysis medium, is suggested. According to the disclosure, an air conditioning device for air conditioning or climatization of a medical treatment device coupled to the media supply arrangement is provided.

By providing the air conditioning device in the media supply arrangement, an air conditioning or climatization of the medical treatment device and in particular the extracorporeal blood treatment device may be achieved, such that thermal loads that are emitted or dissipated into the surroundings and in particular the room air of the treatment room, when common media supply arrangements are used, are conducted at least partially out of the treatment room. Thereby, the air conditioning capacity required for the room air of the treatment room may be reduced, such that the occurrence of draft effects may be reduced.

Due to the arrangement of the air conditioning device in the media supply arrangement, a physical proximity exists between the medical treatment device and the air conditioning device, since the medical treatment device is always placed in the direct surroundings of the media supply arrangement to achieve a supply of the medical treatment device with media.

Due to the physical proximity between the media supply arrangement and the medical treatment device, the air conditioning device may act upon the direct surroundings of the medical treatment device and hence at least partially conduct or remove the thermal loads provided or emitted by the medical treatment device. This removal of the thermal loads from the direct surroundings of the medical treatment device has the effect that the thermal loads are accordingly not, or only to a reduced extent, inputted into the remaining room air, or, in other words, the more remote surroundings of the medical treatment device. Thereby, the indoor climate as sensed by the patient to be treated is not influenced by the thermal loads inputted by the medical treatment device, or are sensed to a reduced extent.

In other words, a local air conditioning or climatization occurs in the surroundings of the media supply arrangement and hence at the same time in the surroundings of the medical treatment device.

The medical treatment device may e.g., be an extracorporeal blood treatment device, such as an apheresis device or a dialysis device, which may be formed or configured, e.g., as a hemodialysis device, hemofiltration device, or as hemodiafiltration device. Dialysis devices are commonly connected to media supply arrangements to achieve a supply e.g., with dialysis water, dialysis concentrate, and/or power. The dialysis devices are accordingly positioned in direct proximity to the media supply arrangement to reduce the lengths of the connecting conduits and connecting cables, and to promote the safety of a workplace by the absence of tripping hazards consisting of conduits. Therefore, a physical proximity exists between the dialysis device and the media supply arrangement.

Preferably, the media supply arrangement comprises a connection for connecting the medical treatment device for feeding a medium to the medical treatment device and/or a drain connection for discharging or removing a medium from the medical treatment device.

Therefore, both an air conditioning or climatization and a required fluid supply are provided for the medical treatment device by the media supply arrangement, also known as media supply panel.

The media supply arrangement may be formed with an individual or own cover panel, such that it may be mounted and integrated into a corresponding recess in a wall or in a wall facing shell. The cover panel in this case covers the recess in the wall or wall-facing shell, such that by means of the cover panel on the one hand closed wall contours may be formed, which is desirable for hygienic reasons and the individual connections and outlets of the media supply arrangement are arranged in a predetermined and preferred arrangement with respect to each other. On the other hand, the recess in the wall or in the wall facing shell may be closed or sealed in an aesthetically appealing manner.

The media supply arrangement may also be formed with its own housing with a cover panel, in which the components of the media supply arrangement are arranged and which may be attached to a wall surface. Thereby, a mounting of the media supply arrangement may also be performed on wall sections, which only permit a limited installation depth.

The media supply arrangement may in a further embodiment also be provided without its own cover panel, such that the individual connections and outlets may then be received in a cover that is present or is to be provided. In this way, an already present impression of a wall portion may be better maintained or the connections and outputs of the media supply arrangement may be more easily integrated in an already present infrastructure.

In order to provide an improved air conditioning, and to configure such air conditioning according to the largest extent of flexibility and adaptable to the respective requirements, the air conditioning device preferably comprises a temperature sensor for measuring the temperature and/or the ambient temperature of the medical treatment device, and wherein a control unit that is communicatively connected with the temperature sensor may be configured to control the air conditioning capacity of the air conditioning device based on a value of the temperature sensor, preferably via a volume flow of a respective ventilator connected to the control unit.

For example, nominal values may be stored in the control unit, which predefine states for the medical treatment device, and wherein actual values are received from the temperature sensor. Upon a deviation of these values, such as when the actual value exceeds the corresponding nominal value, the control unit e.g., controls a volume flow of the air flow in the exhaust air channel provided by the ventilator and, when the media supply arrangement is accordingly formed or configured, also in the supply flow channel, e.g., via the rotational speed of the respective ventilator and preferably with a corresponding adjustment value or actuating value. As such, a temperature that is too high may cause an increase of the air flow while the air flow is reduced in the case of a temperature that is too low. In some embodiments, however, it may also be provided that the sensor only outputs a signal when a threshold is exceeded, wherein the control unit increases the respective air flow or the respective rotational speed of the ventilator to a predefined value.

The temperature sensor may be adapted for the attachment to a medical treatment device and for wireless communication with the control unit, preferably via radio. Accordingly, the temperature sensor may be simply arranged at the medical treatment device and measurement values may e.g., be transmitted via a wireless coupling such as NFC or Bluetooth to the control unit.

Alternatively, the temperature sensor may be connected to the control unit via a cable connection. For this purpose, the temperature sensor may e.g., be formed in the form of a castable thermometer, which comprises a temperature sensor arranged in a sensor housing, which may be connected to the control unit via a flexible cable. Such a castable thermometer may be hung over a part of the medical treatment device, such that it may forward the temperature values in the area of the actual temperature sensor to the control unit via the cable connection.

When using a cable-based temperature sensor, a corresponding connection may be provided on the media supply arrangement, e.g., in the form of a socket, to which a corresponding connection of the temperature sensor or the cable thereof may be coupled or connected, e.g., by means of a plug that is insertable into the socket. The forwarding of the temperature values to the control unit then occurs via the media supply arrangement.

By using a cable-bound temperature sensor the usage of energy sources, e.g., batteries, in the temperature sensor for the delivery of energy for a wireless communication connection may be omitted, such that in this manner a determining of a temperature at a medical treatment device may be achieved with a low radiation and which is reliable and cost-effective. The additionally used cable does not necessarily pose a hindrance, since the medical treatment device is already connected to the media supply arrangement via cables and conduits, such that the presence of a further cable does not significantly carry weight.

By positioning the temperature sensor at or on the medical treatment device, an optimal arrangement or alignment of the medical treatment device with regard to the respective air channel and a reliable direct measurement may be provided. However, alternatively, or in addition, a temperature sensor or temperature probe may also be provided, which is communicatively coupled to the control unit by means of a cable.

Although the temperature sensor provides a reliable measurement value for the required air conditioning or climatization, it may also be provided, alternatively, or in addition, that the control unit is configured to receive an operation parameter of the medical treatment device and to control the air conditioning capacity based on the operation parameter, wherein the operation parameter preferably matches or corresponds to a particular operation mode.

Thereby, an air conditioning may already be provided in an early stage and independently of the measured temperature to e.g., anticipate an upcoming change. For example, a large heat dissipation may result from a hot disinfection of the medical treatment device after the treatment, which significantly heats the room. The operation parameter may in such case be indicative for such a disinfection phase. Accordingly, the control unit may actuate the ventilator with a corresponding actuating value upon receiving such operation parameter to hence remove the heat from the room via the air flow.

Preferably, the air conditioning device comprises an exhaust air channel for discharging or removal of air from the surroundings of the medical treatment device, wherein in particular a first ventilator for discharging air from the surroundings of the medical treatment device into the exhaust air channel is provided. By providing the exhaust air channel in the air conditioning device of the media supply arrangement air may accordingly be sucked from the direct surroundings of the media supply arrangement and hence from the direct surroundings of the medical treatment device to hence at least partially remove or discharge the resulting thermal loads.

Thereby the already present physical proximity between the medical treatment device and the media supply arrangement is again used to discharge the thermal loads of the medical treatment device in a specific or selective manner. It will be understood that also air volumes from the room air may be removed or sucked during the suction of surrounding air that are not influenced by the medical treatment device. The thermal coupling between the media supply arrangement and the medical treatment device is hence not exclusive, but the surrounding air that is influenced by the medical treatment device may nevertheless be sucked or removed to such an extent that a noticeable effect on the remaining room air may be sensed.

By providing the exhaust air channel and the ventilator it is hence enabled that heat may be conducted away from the medical treatment device by means of an air flow. For example, the air flow may be guided either from or at least partially alongside the medical treatment device, wherein the exhaust air channel is preferably configured such that the air flow is discharged from the room in which the medical treatment device is present to the outside, or to a collecting channel.

The heat generated by the medical treatment device is hence discharged or removed from the treatment area. Thereby, the heat input in the treatment room may be reduced, and the air conditioning requirement in the treatment room may hence be reduced. In this manner the indoor climate may be improved, since the thermal loads that are inputted into the treatment room by the operation of the medical treatment device are considerably reduced.

Accordingly, a partial decoupling of the cooling of the medical treatment device from the indoor climate control or room air conditioning may be achieved by the suggested media supply arrangement. This results in a potential reduction of the ventilation or cooling for the patient, such that potential draft effects may also be reduced.

At the same time, the patient is generally situated in proximity of a corresponding medical treatment device. A heat dissipation of the generated heat during normal operation of the medical treatment device is often perceived as unpleasant and may hence also be reduced.

The first ventilator may e.g., be active prior to, during, and/or after the treatment to provide an air flow and hence the corresponding cooling effect. For example, an air flow provided prior to the treatment may result in the provision of a pre-cooling of the medical treatment device, such that, depending on the duration of the treatment, an air flow and accordingly an activation of the ventilator during the treatment may be omitted. Accordingly, a post-treatment cooling may also be provided, e.g., in the case wherein a heat generation particularly occurs at the end of the treatment. Thereby, also noises are reduced during the treatment, which may be perceived as unpleasant for the patient.

The ventilator may either be continuously switched on, or time periods may be predefined for the operation of the ventilator to e.g., reduce the energy consumption. To compensate the volume of the air discharged or removed from the treatment room and to hence avoid pressure differences, it may furthermore be provided that a central supply air is inputted into the room independent of the air conditioning device and either continuously or depending on the central control, e.g., via a conventional ventilation.

To provide an optimal cooling effect, the medical treatment device is preferably positioned on a suitable, predefined utility space. Accordingly, a marked surface may be provided to position the medical treatment device, wherein the exhaust air channel and/or the first ventilator are configured to remove air from the marked utility space and feed said air into the exhaust air channel.

For example, a marking may be provided in the treatment room, which indicates the corresponding utility space and hence the predefined position of the medical treatment device. The medical treatment device may e.g., be positioned before the exhaust air channel and aligned along its air flow. Accordingly, it is ensured that the exhaust air is removed in a decentralized manner and directly from the treatment area to avoid a local accumulation of the heat generated by the blood treatment device and the patient.

Preferably, the air conditioning device comprises a supply air channel for supplying air into the surroundings of the medical treatment device, wherein in particular a second ventilator is provided for supplying air into the surroundings of the medical treatment device.

Accordingly, supply air may be inputted into the room corresponding to the exhaust air in a simple manner, such that the provided air conditioning or cooling effect does not generate pressure differences or an under pressure. Thereby an even better directed air flow may also be provided, which allows a cooling of the medical treatment device.

The avoidance of a development of an under pressure in a treatment room provides a further advantage that unwanted suction effects may be avoided. Such suction effects may pose disadvantages or even hazards e.g., doors may be shut closed and a larger exertion of force may be necessary to open these doors. Particularly for weakened persons or in the potential occurrence of emergency situations, such suction effects may have disastrous consequences. Accordingly, it is particularly preferable to avoid these. In such instance, pressure differences are to be avoided. Furthermore, it is preferred to avoid a relative under-pressure in the treatment room, since an under-pressure may result in germs, e.g., bacteria and viruses, being pushed from the periphery or surroundings into an operation room by the pressure difference. Therefore, an under-pressure is preferably to be avoided in a room from a hygienic perspective.

Furthermore, by means of the introduction of supply air, high quality air is introduced into the room, which may be measured by the air temperature, the $CO_2$ concentration and the relative humidity. To avoid a potential influx of undesirable particles or contaminants a filter may be provided at or in the supply air channel.

The removal or discharge of exhaust air via the exhaust air channel and/or the introduction of supply air via the supply air channel furthermore has the advantage that windows in a treatment room may mainly remain closed and hence, on the one hand, otherwise perceived draft effects may be avoided and, on the other hand, energy may be saved.

Preferably, the respective ventilator is arranged in the respective air channel and the first ventilator is preferably arranged at a first end.

In such an arrangement the media supply arrangement may be kept relatively compact and the efficiency of the ventilator to provide the air flow may be increased. The arrangement of the first ventilator at the first end furthermore has the advantage that air may be sucked into the exhaust air channel and the corresponding suction effect is not reduced by the length of the exhaust air channel.

Preferably, a marking for indicating an installation area for the medical treatment device in the effective range of the air conditioning device is provided.

Accordingly, the medical treatment device may also be formed e.g., to be mobile (i.e., on rollers) and may be positioned in a treatment room at a surface indicated with the marking, such that the medical treatment device is deployable for a patient depending on the treatment requirement and the desired treatment place and only needs to be coupled to the media supply arrangement. Thereby, a fluid required for the treatment may be fed or injected while at the same time a decentralized air conditioning is provided and a desirable, local cooling occurs.

Furthermore, by means of a configuration with at least one drain connection e.g., degradation products or already used fluids may be discharged and may either be stored in the media supply arrangement or may be discharged via a corresponding fluid coupling and via a central fluidic system. The media supply arrangement is hence deployable for a variety of applications.

Preferably, the fluid is a medical liquid, a medical gas, a concentrate, a permeate, a dialysis liquid, a dialysis concentrate, or water. In other words, various liquids required for the treatment of a patient and e.g., for a dialysis may be provided by the media supply arrangement. Medical gases may also be provided, e.g., medical oxygen or gaseous analgesics, such that the media supply arrangement may be deployed for various patient groups and various treatments.

For rooms wherein multiple medical treatment devices are envisaged or present, the media supply arrangement is configured to supply at least two medical treatment devices with media, and wherein for each of the medical treatment devices a separate supply air channel and/or a separate exhaust air channel may be provided, wherein the respective supply air channel or the respective exhaust air channel are preferably coupled to a central exhaust air channel or a central supply air channel.

In some embodiments, at least two connections for the supply of at least two medical treatment devices with at least one medium and/or at least two drain connections for the discharge of at least one medium are provided to supply at least two medical treatment devices with media.

Accordingly, for each medical treatment device at least one fluid connection may be provided, such that e.g., two dialysis devices may be supplied with e.g., dialysate or dialysis liquid.

Preferably, also at least two drain connections are provided, such that the respective dialysis device may e.g., also dispose a retentate or used dialysate.

In cases wherein multiple medical treatment devices are provided in a treatment room, it may furthermore be provided that for each medical treatment device a separate supply air channel and/or a separate exhaust air channel is provided, wherein the respective supply air channel and/or the respective exhaust air channel are preferably coupled to a central exhaust air channel or a central supply air channel.

Preferably, for each medical treatment device both a respective supply air channel and a respective exhaust air channel are provided, such that an improved, separated, and individual air conditioning or climatization is provided.

Particularly in dialysis rooms, multiple dialysis devices are generally present for the simultaneous treatment of multiple patients. To efficiently reduce the heat generated by the respective devices separate air channels are hence provided for each dialysis device. Accordingly, a ventilation or air conditioning by means of the present building technology may be reduced or the additionally generated heat does not need to be compensated therewith. Hence, no undesirable air flows are developed in the room, such that the treatment of a respective patient does not provide an unpleasant indoor climate for the respective patient or the other patients. This effect may be achieved by providing a supply air channel and/or an exhaust air channel for e.g., two dialysis devices, wherein these are arranged at opposing sides of the dialysis devices or wherein the dialysis devices are oriented in opposing directions, e.g., when the components that generate heat are mainly arranged on one side of the respective dialysis device.

The configuration for multiple dialysis devices has the advantage that both for one treatment and also for multiple treatments a desired local air conditioning may be achieved without requiring further media supply arrangements. In other words, also with an arbitrary connection of dialysis devices an air conditioning or climatization and a fluid supply may be achieved, such that a large extent of flexibility is provided.

In some embodiments, the air conditioning device comprises a throttle valve for the mixing of supply air and exhaust air. Accordingly, the possibility exists that supply air is mixed with exhaust air prior to introduction into the intended room. This particularly has the advantage that the air to be introduced may at least partially be tempered or pre-heated, e.g., when for the cooling effect and/or for the patient too cool ambient air is injected. This may also save energy. Furthermore, conversely, the exhaust air may be pre-cooled, e.g., to avoid that the discharged or removed air attains a temperature that is too high, which may e.g., be detrimental for adjacent systems or other components of the medical treatment device.

In some embodiments, the air conditioning device may be directly thermally coupled to the medical treatment device, preferably via a heat conducting element. For example, the heat conducting element may be provided at a first end of the exhaust air channel. The thermal coupling may hence occur via the provided air flow, wherein a heat transfer may also be provided via the provided heat conducting element, such that the heat dissipation may be further improved.

Accordingly, the heat conducting element may form a surface, which receives heat and conducts the heat to an exhaust air channel via the air flow. Furthermore, the heat conducting element may be formed such that the air flow is provided for a predefined surface of the medical treatment device. For example, the heat conducting element may comprise a shape corresponding to the surface, e.g., a cylindrical or conical shape.

To further improve the efficiency of the air conditioning and the heat transfer, the respective air channel is preferably at least partially lined with a thermally isolating material. Hence, it is ensured that the heat is not inadvertently dissipated to the surroundings or into the respective room.

When the media supply arrangement comprises a supply air channel, a corresponding lining may avoid that the cool supply air is heated before it is introduced into the corresponding room. Although the respective channel is preferably lined along the length and circumferentially, it may also be provided that only the ends leading into the room or fluid couplings are thermally isolated, wherein the remaining air channel is e.g., separated from the room or is enclosed by outside air or ambient air.

Preferably, the air conditioning device comprises a silencer, wherein the silencer is preferably arranged at a supply air channel and/or an exhaust air channel and/or a ventilator. To avoid that, the cooling effect causes unpleasant noises a reduction of the noise pollution may be achieved with the silencer. For example, the ventilator may be arranged in the respective air channel, wherein the silencer is attached to the ventilator or adjacent to the ventilator at the air channel.

For a more accurate control of the air conditioning, the media supply arrangement may furthermore comprise a humidity sensor, a $CO_2$-sensor, and/or a flow sensor, wherein the sensor is arranged in the respective air channel and is communicatively connected to the control unit. In this case, the control unit is configured to control the respective volume flow based on the value of the sensor.

This particularly has the advantage that the air to be introduced may be adapted to the required indoor climate. For example, the control unit may cause that the volume flow in the exhaust air channel is increased when a $CO_2$ concentration is measured that is too high, such that the air that is present in the room is conducted away from the treatment area or from the medical treatment device, wherein at the same time an increase in the volume flow in the supply air channel causes the introduction of fresh air, e.g., outside air. Accordingly, a configuration with an exhaust air channel may already lead to the desired reduction of the $CO_2$ concentration, wherein a configuration with a supply air channel has the synergistic effect that simultaneously an inflow of $CO_2$ depleted air is provided.

By means of the flow sensor it may furthermore be ensured that a sufficient fresh air supply is provided, e.g., by increasing the volume flow in the supply air channel when the received measurement value is too low. However, a measurement value that is too high may also be perceived by a patient as unpleasant, such that a volume flow may be reduced in such case.

In order to control the characteristics of the supplied air in a further flexible manner, it may furthermore be provided that at least one air channel, preferably each air channel, comprises a heating element, a cooling element, a humidification element, and/or a dehumidification element, which is communicatively connected to the control unit, wherein the control unit is configured to control the temperature and/or the humidity of the respective air flow based on the respective value of the sensor.

Accordingly, the volume flow may not only be controlled in the case of a deviation from a nominal value, but the air characteristics may be directly adapted to the desired characteristics or conditions. For example, the performed climatization may be dependent on the respective weather situation or season of the year, in particular when e.g., outside air is used for the supply air. As such, an after-cooling may be required for the climatization of the respective treatment device in summer while in winter a humidification of the air may provide an improved breathing air for the respective patient.

Alternatively, or in addition to the sensor based control of the respective air flows, the media supply arrangement may also comprise an operating element, which is communicatively connected to the control unit and is configured to set a nominal value of the temperature, the respective volume flow, the $CO_2$ concentration, and/or the relative humidity.

For example, the operating element may be formed as a remote control, which is connected with the control unit, such that a patient or a user may manually set the respective nominal value and dependent on the desired characteristics.

In some embodiments, a wireless operating element is provided to set the temperature, the flow, and/or the relative humidity and which is communicatively connected to the control unit, preferably via radio, WLAN, Bluetooth, Zigbee, NFC, Wi-Fi, RFID, or infrared, wherein the operating element is preferably formed as a terminal device, preferably as a smartphone, smartwatch or tablet, and wherein the control unit is preferably configured to set a nominal value based on an identification of a user.

For example, a patient may hence simply perform a setting of the air conditioning device and in particular of the volume flow of the respective ventilator via a present terminal device such as a smartwatch or tablet, wherein the control unit controls the volume flow based on the performed setting or adjustment and on a status of the respective ventilator, e.g., based on a measured flow, by means of an adjustment value or actuating value.

To set or adjust the nominal value, a coupling of the terminal device with the control unit is preferably required, which may be performed via a corresponding login. Such login may be provided by a manual user input or also automatically, e.g., via an automatic emitting of an identification, e.g., a patient identification or of the medical personnel, preferably via NFC or via RFID. Both the user identification and the respective settings may furthermore be stored in the terminal device and/or the control unit, such that a repeated entry or input is not required for future applications in a dialysis system.

The media supply arrangement hence provides a plurality of possibilities to provide both a desired, improved climatizing or air conditioning and a technical interface for a medical treatment device, when needed.

In some embodiments, the air conditioning device provides an air conditioning connection, to which a medical treatment device to be air conditioned is connectable. Thereby, for example, cold may be introduced directly into the medical treatment device to achieve a direct cooling in this manner. The medical treatment device may accordingly be connected to a cooling circuit that is provided at the media supply arrangement to be accordingly cooled. The cooling medium provided at the air conditioning connection may be either air or another cooling medium, e.g., cooling water.

The above objectives and advantages are furthermore achieved by a medical treatment system with at least one medical treatment device, preferably with a hemodialysis device, a hemofiltration device, a hemodiafiltration device, or an apheresis device. According to the disclosure, at least one media supply arrangement with an air conditioning device as described in the above is provided.

BRIEF DESCRIPTION OF THE DRAWINGS

Preferred further embodiments of the disclosure will be explained in more detail by the following description of the Figures, in which it is shown.

DETAILED DESCRIPTION OF EXAMPLE EMBODIMENTS

Figure 1:
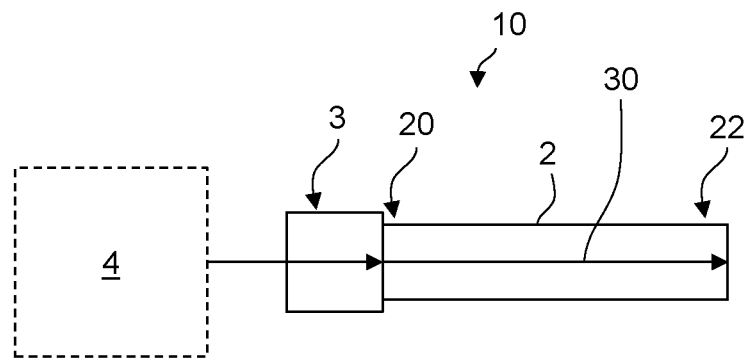
FIG. 1 is a schematic view of the functioning of an air conditioning device with an exhaust air channel.

In the following, the disclosure will be explained in more detail with reference to the accompanying Figures. In the Figures, like elements are denoted by identical reference numerals and repeated description thereof may be omitted in order to avoid redundancies.

In FIG. 1, an air conditioning device 10 is schematically shown, which provides a zone specific climatization or air conditioning for a treatment room having one or more medical treatment devices arranged therein. The air conditioning device 10 is arranged in a media supply arrangement for supplying the medical treatment device with at least one medium, which is not completely shown in this Figure. The medical treatment device may e.g., be a dialysis device, which is connected via suitable interfaces with the media supply arrangement for supplying the dialysis device with e.g., dialysis, water, concentrate, and/or power. The media supply arrangement will be explained in more detail below.

The medical treatment device is schematically depicted by the dashed area in the Figure.

The air conditioning device 10 comprises, in the presently shown embodiment, an exhaust air channel 2 as well as an attached ventilator 3. The ventilator 3 is arranged at a first end 20 of the exhaust air channel 2, and is configured to feed air in the exhaust air channel 2 from the first end 20 to a second end 22 such that an airflow 30 is accordingly provided (indicated with the arrow).

The airflow 30 hence comprises air, which is sucked by the first ventilator 3 into the exhaust air channel 2 and thereby feeds surrounding air from the surroundings of the first ventilator 3 or from the surroundings of the first end 20 of the exhaust air channel 2 (as also indicated with the arrow).

Due to this arrangement and alignment of the ventilator 3 and the first end 20 of the exhaust air channel 2, surrounding air may hence be specifically received from a particular area of the treatment room and may be discharged or removed from the treatment room via the exhaust air channel 2. For this purpose, the second end 22 is preferably connected with the outside air and may accordingly be connected to a central accumulation channel.

Alternatively, or in addition, the second end 22 may be coupled to other air channels by a connecting channel, such that the exhaust air discharged by the air flow 30 may span larger distances than the exhaust air channel 2.

Since the airflow 30 receives surrounding or ambient air, and since this occurs selectively due to the arrangement and alignment of the ventilator 3 or the exhaust air channel 2, air may be removed or discharged from a medical treatment device 4 that is adjacent to the first ventilator 3 or to the first end 20 of the exhaust air channel.

The medical treatment device 4 is not part of the air conditioning device 10, as indicated by the dashed lines, however, it may optionally be part of a corresponding treatment system. Depending on the operation mode of the medical treatment system 4, heat may be generated which causes a local heating of the surrounding or ambient air. For example, it is required that, in the case of a medical treatment device in the form of a dialysis device, the dialysis medium is heated, for which purpose a corresponding heating device needs to be present in the dialysis device. The heat generated during the process of heating the dialysis medium may be removed or discharged by the suggested air conditioning device 10. For example, the surrounding air or heat may be selectively removed by the ventilator 3 and the exhaust air channel 2, such that accordingly a local, decentralized air conditioning or climatization is provided for the medical treatment device 4.

The ventilator 3 may be continuously switched on and may thereby also provide a continuous volume flow of the air flow 30. However, optionally, it may also be provided that the ventilator 3 is only switched on after a predefined operation time to hence e.g., save energy or to consider treatment times.

Figure 2:
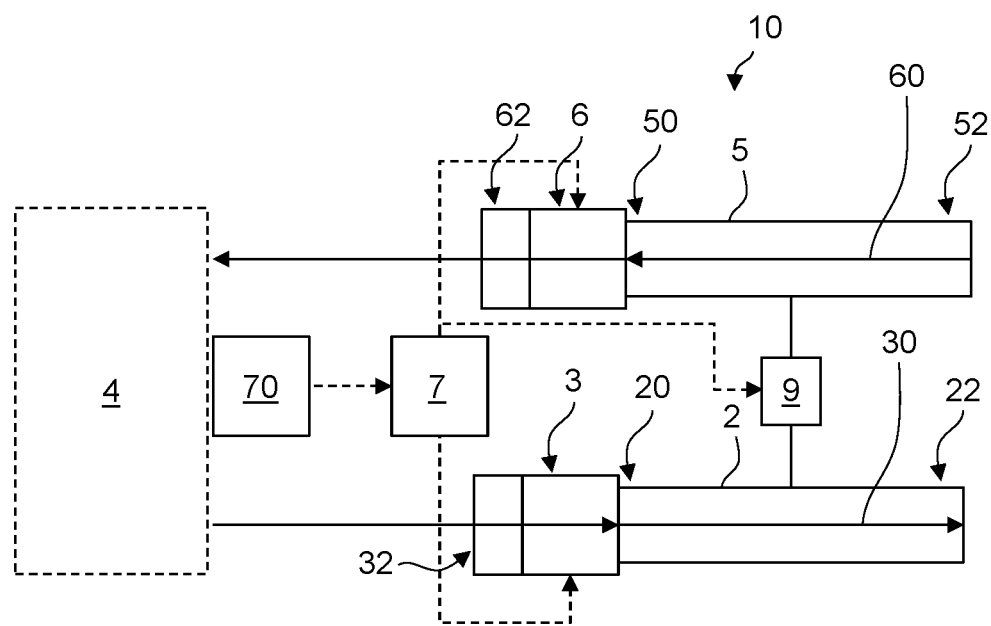
FIG. 2 is a schematic view of an air conditioning of an extracorporeal blood treatment device with a supply air channel and a control unit.

In FIG. 2, a schematic depiction of the air conditioning device 10 according to FIG. 1 is shown, wherein the air conditioning device 10 is arranged in a media supply arrangement that is not shown in detail and wherein, in addition, a supply air channel 5 is provided. As for the exhaust air channel 2 a second ventilator 6 is provided for the supply air channel 5, which is arranged at a corresponding first end 50 of the supply air channel 5.

The second ventilator 6, however, functions in the exact opposite direction, such that supply air is fed from a corresponding second end 52 of the supply air channel 5 to its first end 50 and a corresponding air flow 60 is provided (as indicated with the arrow). Accordingly, supply air is introduced into the room, which is mixed with the surrounding air (as also indicated with the arrow).

As shown in FIG. 1, a medical treatment device 4 is also provided in the embodiment according to FIG. 2, which is positioned in regard to the air conditioning device 10 and hence also in regard to the media supply arrangement such that it is aligned with the respective first end 20, 50 of the exhaust air channel 2 and the supply air channel 5. However, alternative arrangements are possible, wherein the medical treatment device 4 is e.g., aligned in closer proximity to the first end 50 of the supply air channel 5 to provide an impingement cooling and wherein optionally, the first ventilator may comprise a corresponding higher rotation speed to provide a sufficient suction force.

A silencer 32, 62 may be attached to each ventilator, such that the additional air introduction or extraction does not cause any unpleasant noises for the patient to be treated.

Furthermore, a control unit 7 is provided which is connected to the ventilators 3, 6, and controls a respective volume flow through the respective air channel by means of a corresponding setting of the rotation speed (as indicated with the dashed arrows). The control unit 7 is communicatively connected with a temperature sensor 70, wherein the temperature sensor 70 is attached to the medical treatment device 4.

The temperature sensor 70 is configured to transmit the corresponding measurement values wirelessly to the control unit 7, as indicated with the dashed arrow, in the present example via Bluetooth. However, also other wireless communication connections may be chosen, as described in the above. The temperature sensor 70 may either be battery powered or may be connected to a power supply of the medical treatment device 4 via a corresponding electrically conducting connection.

In an alternative not explicitly shown in the Figures, the temperature sensor 70 may also be connected with the control unit 7 via a cable connection. To this end the temperature sensor 70 may e.g., be formed as a castable thermometer, which e.g., comprises a temperature sensor 70 arranged in a sensor housing and which may be connected to the control unit 7 via a flexible cable. Such a castable thermometer may then be hung over a part of the medical treatment device 4 such that it forwards the temperature values measured in the area of the actual temperature sensor 70 via the cable connection to the control unit 7.

When using a cable-based temperature sensor 70 a corresponding connection may be provided on the media supply arrangement, e.g., in the form of a socket, to which a corresponding connection of the temperature sensor 70 or the cable thereof may be coupled or connected, e.g., by means of a plug that is insertable into the socket. The forwarding of the temperature values to the control unit 7 then occurs via the media supply arrangement.

By using a cable-bound temperature sensor 70, the usage of energy storage sources, e.g., batteries, in the temperature sensor 70 for the delivery of energy for a wireless communication connection may be omitted, such that in this manner a determining of a temperature at a medical treatment device may be achieved with a low radiation and which is reliable and cost-effective. The additionally used cable does not necessarily pose a hindrance, since the medical treatment device is already connected to the media supply arrangement via cables and conduits, such that the presence of a further cable does not significantly carry weight.

The control unit 7 hence receives the measured temperature values of the medical treatment device 4. In the control unit 7 corresponding nominal values are stored, which are compared to the received actual values, wherein the control unit 7 outputs a corresponding actuation value or adjustment value to accordingly change the rotation speed of the respective ventilator 3, 6.

Thereby, a more accurate air conditioning is enabled by the control unit 7 and the temperature sensor 70, wherein the supply air and the exhaust air provide a local cooling of the medical treatment device 4 according to the set volume flow.

In addition, a throttle valve 9 is provided between the exhaust air channel 2 and the supply air channel 5, which is also controlled by the control unit 7 (as indicated with the dashed arrow).

The throttle valve is closed in normal operation, however, may be opened in intermediate periods to e.g., mix exhaust air with supply air, and hence provides an after-cooling prior to the discharge to e.g., outside air or adjacent systems. The throttle valve 9 may also preheat the supply air, e.g., when cold outside air is introduced in winter and is either perceived as to cold or may be detrimental for the respective components or for the medical treatment, e.g., since cold outside air may lead to an increased condensation of humidity at undesirable positions or in more extreme cases to a freezing of movable parts.

Figure 3:
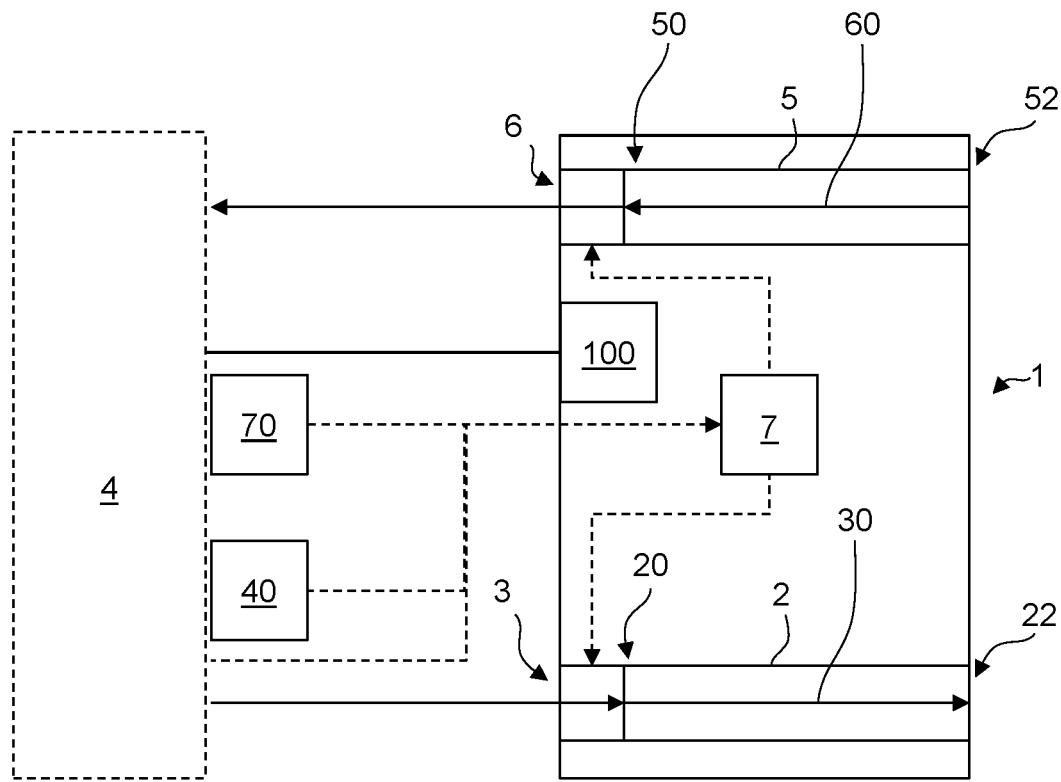
FIG. 3 is an embodiment of a media supply arrangement with an air conditioning device.

The embodiment according to FIG. 3 essentially corresponds to the embodiment according to FIG. 2, although a throttle valve is not explicitly provided, however, may optionally be possible. Both the supply air channel 5 and the exhaust air channel 2 as well as the corresponding ventilators 3, 6 and the control unit 7 are arranged in the media supply arrangement 1 according to FIG. 3.

The media supply arrangement 1 serves to supply a medical treatment device 4 with the corresponding operation media. The medical treatment device 4 is therefore connected to the media supply arrangement 1 via corresponding interfaces that may be e.g., media specific.

By means of the media supply arrangement 1, a medical treatment device 4 configured as e.g., a dialysis device may be supplied with dialysis water, dialysis concentrate, and power. Furthermore, also a drain conduit for a used dialysis liquid may be provided. A coupling of the medical treatment device to the media supply arrangement 1 occurs e.g., via tubes and cables at corresponding interfaces of the media supply arrangement 1, which in the present embodiment are coupled to the media supply arrangement 1 via connections 100.

The media supply arrangement 1 may be formed with an individual or own cover panel, such that it may be mounted or integrated in a corresponding recess of a wall or in a wall facing shell. The cover panel thereby covers the recess in the wall or the wall facing shell, such that by means of the cover panel, on the one hand, closed or continuous wall contours may be formed, which is desirable for hygienic reasons and the individual connections and outlets of the media supply arrangement 1 are arranged in a predetermined and preferred arrangement with respect to each other. On the other hand, the recess in the wall or in the wall facing shell may be closed or sealed in an aesthetically appealing manner.

The media supply arrangement 1 may also be formed with its own housing, in which the components of the media supply arrangement 1 are arranged and which may be attached to a wall surface. Thereby, a mounting of the media supply arrangement may also be performed on wall sections, which only permit a limited installation depth.

The media supply arrangement 1 may in a further alternative also be provided without its own cover panel, such that the individual connections and outlets may then be received in a cover that is present or is to be provided. In this way, an already present impression of a wall portion may be better maintained or the connections and outputs of the media supply arrangement 1 may be more easily integrated in an already present infrastructure.

By means of the connection 100, the medical treatment device 4 may accordingly be supplied with a fluid, in particular with a medical liquid. The medical treatment device 4 is presently formed as a dialysis device, wherein the fluid provided by the connection 100 of the media supply arrangement 1 may be a dialysis liquid. However, other liquids, in particular medical liquids, concentrates, and/or water may also be provided. Although not shown in FIG. 3, also multiple connections 100 may be provided for the respective fluids.

Furthermore, as already mentioned, also a supply of energy in the media supply arrangement 1 may occur e.g., via a power connection.

The ventilators 3, 6 according to FIG. 3 are arranged in the respective air channel, such that the air conditioning device 10 and in particular the media supply arrangement 1 may be formed in a compact manner. The arrangement within the respective air channel furthermore has the advantage that the efficiency may be increased and, at the same time, noise may already be minimized based on the arrangement and the silencing by the media supply arrangement 1. However, silencers (not shown) may additionally be provided.

The control unit 7 is furthermore communicatively connected to the medical treatment device, as shown with the corresponding dashed arrow. Accordingly, the control unit 7 is configured to receive an operation parameter from the medical treatment device. This at least has the advantage that the control unit 7 receives information regarding the operation mode, such that the control of the ventilators 3, 6 not only occurs based on the measured temperature, but also dependent on the determined operation mode.

For example, a disinfection of the medical treatment device by means of a hot disinfection may take place at the end of the treatment, which significantly heats the surrounding temperature. However, by the corresponding communication with the control unit 7, it is ensured that the volume flow of the exhaust air and the supply air is already increased, such that a sudden heating may be anticipated and the patient hence does not perceive an unpleasant temperature increase of the surrounding air.

Furthermore, in some embodiments an operating element 40 in the form of a smart phone is provided by which the patient or other user may input a setting of the desired temperature or volume flow. The smart phone is accordingly wirelessly connected to the control unit 7, preferably via NFC or RFID, such that a user identification and also a corresponding login occur automatically. Based on the user input and the measured temperature a corresponding actuation value is inputted by the control unit 7 and the volume flow in the respective air channel is accordingly controlled.

Figure 4:
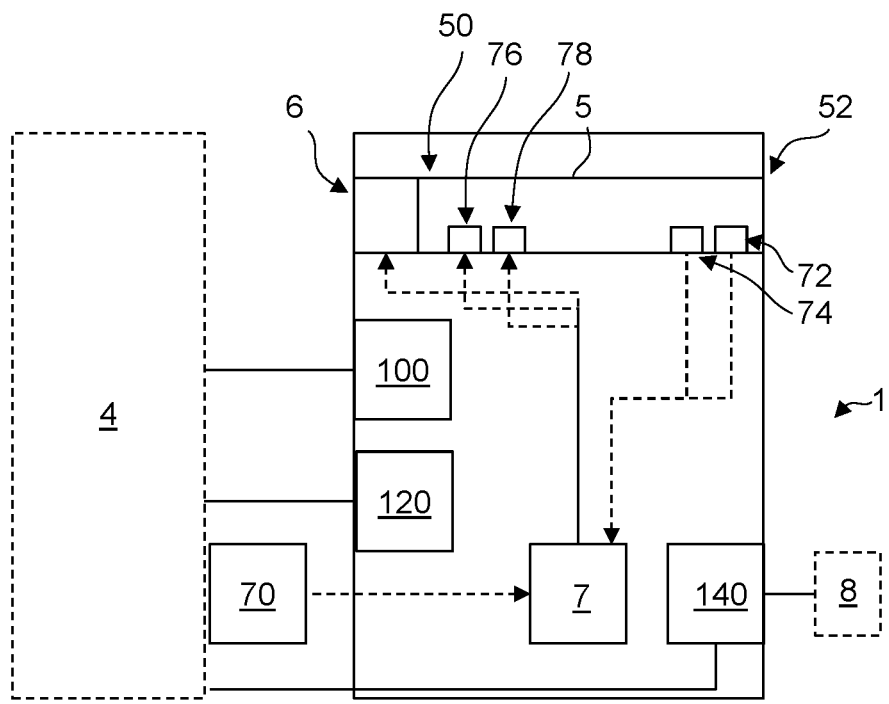
FIG. 4 is a partial schematic view of the embodiment according to FIG. 3 with alternative connections and sensors.

In FIG. 4, a partial view of the embodiment according to FIG. 3 is schematically shown, wherein corresponding features of the exhaust air channel and the details of the supply air channel 5 have merely been committed for an improved overview.

Further sensors are arranged in the supply air channel 5, which measure characteristics of the introduced supply air. In the depicted embodiment, a further temperature sensor 72, and a humidity sensor 74 are provided that accordingly forward measurement values to the control unit 7, as indicated with the dashed arrows. To control the corresponding characteristics of the supply air, a cooling element 76 and a humidification element 78 are furthermore provided in the supply air channel 5, which are actuated by the control unit 7 based on the respective measured values. The control unit 7 accordingly outputs an adjustment value or actuation value that is based on a comparison of the received actual value with a stored nominal value.

Thereby, e.g., warm outside air, for example, in summer, may be accordingly pre-cooled, such that a sufficient cooling or air conditioning or climatization of the coupled extracorporeal blood treatment device for may be achieved. By the same token, a humidification may be particularly provided in winter for dry outside air, such that at the same time pleasant breathing air is provided for the patient. However, further sensors may also be provided, e.g., flow sensors or $CO_2$ sensors, and the arrangement is not limited with regard to the supply air channel 5, but may also be provided in the exhaust air channel.

In addition to the fluid connection or fluid supply connection 100, a drain connection 120 is furthermore provided by which fluids from the medical treatment device 4 may be discharged and disposed. For example, fluids such as used dialysate or retentate or also calibration liquids may hence be disposed in a simple manner without requiring further modifications of the arrangement of the medical treatment device 4 in regard to the media supply arrangement 1. Hence, it is ensured that an intended zone based climatization or air conditioning may be achieved.

Furthermore, in the depicted embodiment an electric module 140 is provided in the media supply arrangement 1, which connects the medical treatment device 4 with a power supply 8. This provides the advantage that a power supply may be guaranteed at any time point and a user is not dependent on longer power cables or the presence of corresponding sockets. The media supply arrangement is hence to a large extent autonomous and provides the security that a newly positioned medical treatment device 4 may be supplied with the desired media for the treatment.

Figure 5:
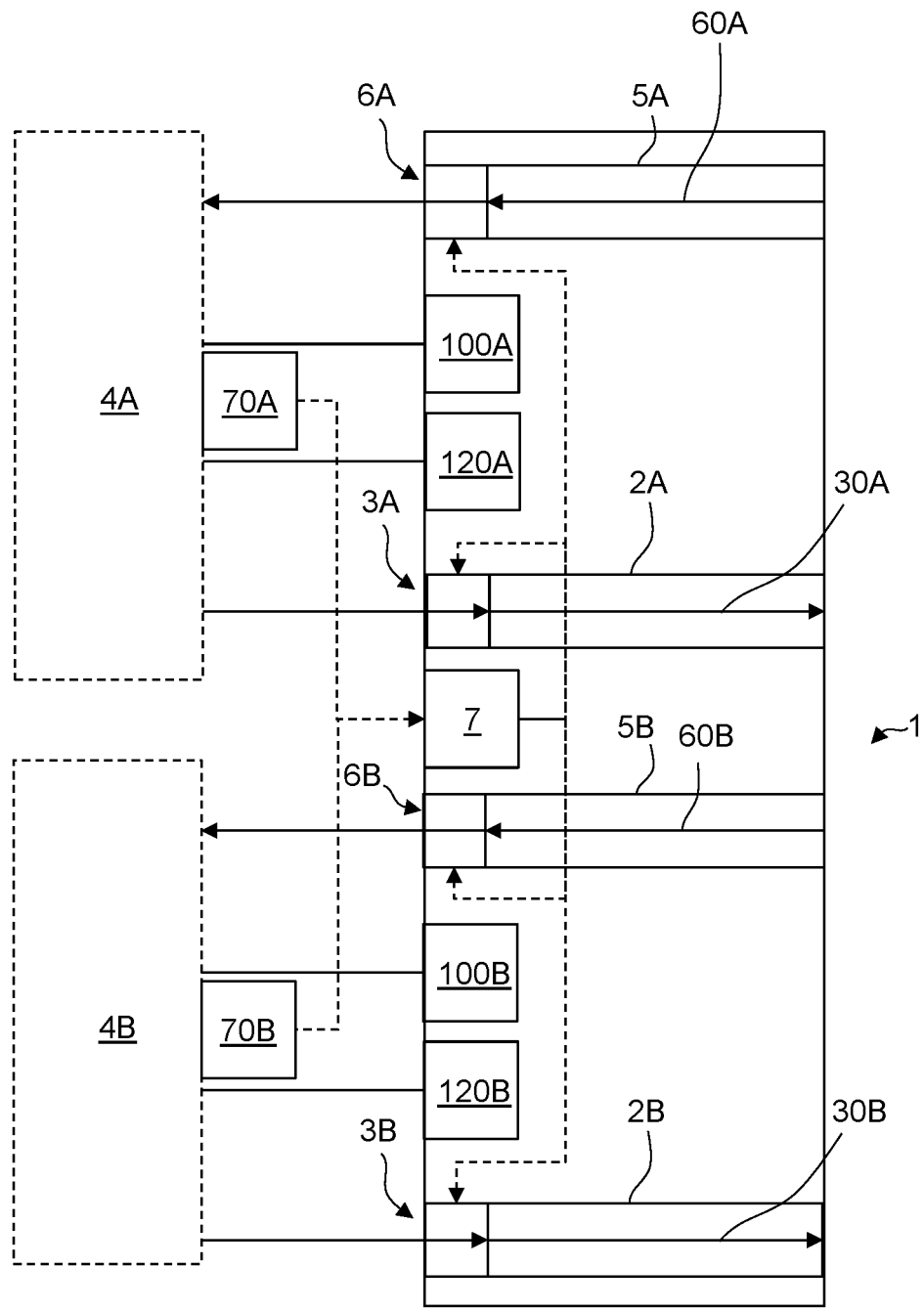
FIG. 5 is a schematic view of a media supply arrangement for two extracorporeal blood treatment devices.

In FIG. 5, a media supply arrangement 1 for two medical treatment devices 4A, 4B is schematically shown, which are here configured as dialysis devices. With the exception of the respective temperature sensors 70A, 70B, all components of the media supply arrangement 1 and in particular of the air conditioning device are arranged in the media supply arrangement 1.

Accordingly, for each coupled dialysis device, a supply air channel 5A, 5B is provided with a corresponding ventilator 6A, 6B for providing a respective airflow 60A, 60B. In an analogous fashion, the media supply arrangement 1 also comprises an exhaust air channel 2A, 2B with a corresponding ventilator 3A, 3B for providing a respective air flow 30A, 30B. The ventilators 3A, 3B, 6A, 6B are thereby communicatively coupled to the control unit 7, such that the control unit 7 may set or control the corresponding volume flow based on the received measurement value of the respective temperature sensor 70A, 70B.

The configuration for two dialysis devices hence has the advantage that the dialysis system only requires a control unit 7, and the media supply arrangement 1 may hence be more compactly formed and without redundancies.

The supply air channels 5A, 5B and exhaust air channels 2A, 2B are furthermore arranged such that a climatization or air conditioning of the connected dialysis device may be provided. To simplify this and to accordingly arrange or align the corresponding dialysis device, markings may furthermore be provided (not shown), e.g., on the floor of a dialysis room, which indicate the correct positioning and hence facilitate the preparation of the treatment and potentially a correction of the climatization or air conditioning.

Furthermore, for each dialysis device, a fluid connection 100A, 100B and a drain connection 120A, 120B are provided such that the respective dialysis device is supplied with the required fluid and a used or consumed fluid may accordingly be discharged or disposed of. Accordingly, the respective connections may be connected with a central fluidic system or a reservoir with a corresponding fill level indicator indicating the present fluid may be provided.

The configuration for two medical devices 4A, 4B furthermore has the advantage that the media supply arrangement 1 may provide a required individual and local climatization or air conditioning already with one connected medical treatment device, yet in addition, depending on the requirements, a further medical treatment device may be connected to e.g., treat a further patient. Also in this case, an individual and local climatization or air conditioning is provided, such that the heat generation of a medical treatment device does not influence the surrounding air of the other medical treatment device or only to a negligible extent. Accordingly, local changes of the surrounding air may also be counteracted locally without requiring a central climatization or air conditioning.

The air conditioning or climatization provided by the air conditioning device or climatization device is shown in the previously described embodiments with regard to a medical treatment device, wherein the medical treatment device is not part of the media supply arrangement 1.

However, it may be optionally provided that the media supply arrangement 1 is formed as an additional module for a medical treatment device for, e.g., for an extracorporeal blood treatment device, for example, as a separate but connectable and coupable unit, such that these together form a common system. Accordingly, e.g., a dialysis system may be optionally provided which comprises both an extracorporeal blood treatment device and the media supply arrangement as described in the above.

Where applicable, all individual features that are shown in the various embodiments may be combined with each other and/or be replaced without leaving the scope of the disclosure.

LIST OF REFERENCE NUMERALS

1 Media supply arrangement
10 Air conditioning device
100 Fluid supply connection
100A, 100B Fluid supply connection
120 Drain connection
120A, 120B Drain connection
140 Electric module
2 Exhaust air channel
2A, 2B Exhaust air channel
20 First end
22 Second end
3 First Ventilator
3A, 3B First Ventilator
30 Air flow
30A, 30B Air flow
32 Silencer
4 Medical treatment device
4A, 4B Medical treatment device
40 Operating element
5 Supply air channel
5A, 5B Supply air channel
50 First end
52 Second end
6 Second Ventilator
6A, 6B Second Ventilator
60 Air flow
60A, 60B Air flow
62 Silencer
7 Control unit
70 Temperature sensor
70A, 70B Temperature sensor
72 Temperature sensor
74 Humidity sensor
76 Cooling element
78 Humidification element
8 Power supply
9 Throttle valve

The invention claimed is:

1. A media supply arrangement configured to supply an extracorporeal blood treatment device with a dialysis medium, wherein:
the media supply arrangement is enclosed in (i) a corresponding recess in a wall or (ii) a recess in a wall facing shell by means of a cover panel that covers the recess; and
the media supply arrangement comprises a decentralized air conditioning device, the decentralized air conditioning device comprising:
an exhaust air channel configured to discharge air from surroundings of the extracorporeal blood treatment device; and
a first ventilator for discharging air from the surroundings of the extracorporeal blood treatment device into the exhaust air channel, wherein the decentralized air conditioning device is configured to selectively remove locally heated air surrounding the extracorporeal blood treatment device by means of the exhaust air channel and the first ventilator in a connected state of the media supply arrangement with the extracorporeal blood treatment device.

2. The media supply arrangement according to claim 1, further comprising a connection for connecting the extracorporeal blood treatment device for feeding a medium to the extracorporeal blood treatment device, and/or a drain connection for discharging a medium from the extracorporeal blood treatment device.

3. The media supply arrangement according to claim 1, wherein the decentralized air conditioning device comprises a temperature sensor for measuring a temperature and/or an ambient temperature of the extracorporeal blood treatment device, and wherein a control unit that is communicatively connected with the temperature sensor is configured to control the air conditioning capacity of the decentralized air conditioning device based on a value of the temperature sensor.

4. The media supply arrangement according to claim 3, wherein the control unit is configured to be communicably coupled to the extracorporeal blood treatment device and the control unit is configured to receive a signal comprising an operation parameter of the extracorporeal blood treatment device and to control the air conditioning capacity based on the operation parameter.

5. The media supply arrangement according to claim 1, wherein the decentralized air conditioning device comprises:
a supply air channel configured to supply air into surroundings of the extracorporeal blood treatment device; and
a second ventilator configured to supply air into the surroundings of the extracorporeal blood treatment device.

6. The media supply arrangement according to claim 1, wherein a marking for indicating an installation area for the extracorporeal blood treatment device in an effective range of the decentralized air conditioning device is provided.

7. The media supply arrangement according to claim 1, wherein:
the media supply arrangement is configured to supply media to at least two extracorporeal blood treatment devices via respective fluid supply conduits the decentralized air conditioning device comprises a respective supply air channel for each of the at least two extracorporeal blood treatment devices and/or a respective exhaust air channel for each of the at least two extracorporeal blood treatment devices.

8. The media supply arrangement according to claim 1, wherein the decentralized air conditioning device comprises a throttle valve for mixing of supply air and exhaust air.

9. The media supply arrangement according to claim 1, wherein the decentralized air conditioning device is configured to be directly thermally coupled to the extracorporeal blood treatment device.

10. The media supply arrangement according to claim 1, wherein the decentralized air conditioning device comprises a silencer.

11. The media supply arrangement according to claim 1, wherein at least one air channel of the decentralized air conditioning device comprises a heating element, a cooling element, a humidification element, and/or a dehumidification element which is communicatively connected to a control unit, and wherein the control unit is configured to control the temperature and/or the humidity of the respective air flow based on one or more signals received from a humidity sensor or a temperature sensor.

12. The media supply arrangement according to claim 1, wherein the decentralized air conditioning device is adjustable via a wireless operating element a smartphone, a smartwatch, or a tablet, and wherein the decentralized air conditioning device sets a nominal value based on an identification of a user.

13. The media supply arrangement according to claim 1, wherein the decentralized air conditioning device provides an air conditioning connection to which the extracorporeal blood treatment device to be air conditioned is connectable.

14. A medical treatment system comprising:
the media supply arrangement according to claim 1; and
the extracorporeal blood treatment device.

15. The medical treatment system of claim 14, wherein the extracorporeal blood treatment device is a hemodialysis device, a hemofiltration device, a hemodiafiltration device, or an apheresis device.

16. The media supply arrangement according to claim 3, wherein the control unit is configured to control a volume flow of a respective ventilator connected to the control unit based on the value of the temperature sensor.

17. The media supply arrangement according to claim 4, wherein the operation parameter comprises a particular operation mode.

18. The media supply arrangement according to claim 7, wherein the respective supply air channel or the respective exhaust air channel is configured to be coupled to a central exhaust air channel or a central supply air channel.

19. The media supply arrangement according to claim 9, wherein the decentralized air conditioning device is configured to be directly thermally coupled to the extracorporeal blood treatment device via a heat conducting element.

20. The media supply arrangement according to claim 10, wherein the silencer is arranged at a supply air channel, an exhaust air channel, and/or a ventilator.

21. The media supply arrangement according to claim 11, wherein each air channel of the decentralized air conditioning device comprises a heating element, a cooling element, a humidification element, and/or a dehumidification element which is communicatively connected to the control unit.

22. The media supply arrangement according to claim 12, wherein the wireless operating element is via radio, WLAN, Bluetooth, Zigbee, NFC, Wi-Fi, RFID, or infrared.

23. The media supply arrangement according to claim 12, wherein the wireless operating element is formed as a terminal device.

24. The media supply arrangement according to claim 23, wherein the terminal device comprises a smartphone, smartwatch or tablet.

25. The medical treatment system of claim 14, wherein, in the connected state of the media supply arrangement with the extracorporeal blood treatment device, a first end of the exhaust air channel and/or the first ventilator is adjacent to the extracorporeal blood treatment device.

* * * * *